United States Patent
Roos et al.

(10) Patent No.: US 8,223,984 B2
(45) Date of Patent: Jul. 17, 2012

(54) SYSTEM FOR FORMING A HEARING PROTECTOR, EAR CUP IN SUCH A SYSTEM, AND HEARING PROTECTOR FORMED BY SUCH A SYSTEM

(75) Inventors: Anders Roos, Värnamo (SE); Joakim Birgersson, Vetlanda (SE); Håkan Davidsson, Värnamo (SE)

(73) Assignee: MSA Sordin AB, Värnamo (SE)

( * ) Notice: Subject to any disclaimer, the term of this patent is extended or adjusted under 35 U.S.C. 154(b) by 291 days.

(21) Appl. No.: 12/526,294

(22) PCT Filed: Feb. 6, 2008

(86) PCT No.: PCT/SE2008/000098
§ 371 (c)(1),
(2), (4) Date: Sep. 10, 2009

(87) PCT Pub. No.: WO2008/100197
PCT Pub. Date: Aug. 21, 2008

(65) Prior Publication Data
US 2010/0128885 A1 May 27, 2010

(30) Foreign Application Priority Data
Feb. 14, 2007 (SE) .................... 0700371

(51) Int. Cl.
*A61F 11/06* (2006.01)

(52) U.S. Cl. .......... 381/72; 381/71.6; 381/71.7; 381/74; 381/353; 381/372; 381/370

(58) Field of Classification Search .............. 381/72, 381/71.6, 71.7, 74, 353, 372, 370
See application file for complete search history.

(56) References Cited

U.S. PATENT DOCUMENTS
5,551,089 A   9/1996 Whidden
6,735,316 B1 * 5/2004 Wurtz ................ 381/74

FOREIGN PATENT DOCUMENTS
EP    0967592 A2   12/1999
GB    2279202 A    12/1994
WO    03019978 A2   3/2003

OTHER PUBLICATIONS
International Search Report dated May 23, 2008 in corresponding international patent application No. PCT/SE2008/000098, 3 pages.

* cited by examiner

*Primary Examiner* — Vivian Chin
*Assistant Examiner* — Paul Kim
(74) *Attorney, Agent, or Firm* — Maier & Maier, PLLC

(57) ABSTRACT

A system for forming hearing protectors, an ear cup of such a system and a hearing protector formed from such a system. The system includes a number of first ear cups and a number of second ear cups, the first and second ear cups having noise-reducing spaces of different size, and at least one electronic unit with at least one speaker. This system allows the same type of electronic unit to be used for ear cups with different degrees of noise attenuation.

10 Claims, 4 Drawing Sheets

SYSTEM FOR FORMING A HEARING PROTECTOR, EAR CUP IN SUCH A SYSTEM, AND HEARING PROTECTOR FORMED BY SUCH A SYSTEM

RELATED APPLICATIONS

The present invention claims priority under 35 U.S.C. §119 to Swedish Patent No. 0700371-8, filed on Feb. 14, 2007, the disclosure of which is incorporated by reference herein in its entirety.

FIELD OF THE INVENTION

The present invention relates to a system for forming hearing protectors, a hearing protector formed from such a system, and ear cups adapted for use in a hearing protector formed from such a system. More specifically, the invention concerns hearing protectors that in addition to a noise-reducing function also have a sound-reproducing function associated with the hearing protector to allow the emission of sound inside the hearing protector.

TECHNICAL BACKGROUND

Hearing protectors comprise two ear cups and a device for fastening the hearing protector to the head of a wearer, such that the ear cups are positioned over the wearer's ears. Ear cups used in existing hearing protectors may function as active elements, which means that they have a passive, sound-reducing function which is combined with the function of actively reproducing sound inside the ear cup to allow the user to hear this reproduced sound.

To this end, the ear cup may be provided with an electronic unit having a speaker. The electronic unit may incorporate different functions. One type of electronic unit may, for instance, contain a radio receiver and the electronic circuitry required to reproduce the sound received by the radio receiver through the speaker. Another type of electronic unit may be designed such that it is capable of reproducing ambient sound from the vicinity of the hearing protector. In this case, the hearing protector may be provided with a microphone that is connected to the electronic unit. The electronic unit thus has a function that allows it to receive the sound from the microphone and convert it in such a manner that it is emitted by the speaker in the ear cup at a level that is suitable for the wearer. The electronic circuitry of the electronic unit may comprise, for example, circuits that dampen frequencies that are particularly disturbing to the human ear for the benefit of the frequency range within which ordinary speech is situated. In this way, the user of an active hearing protector of this kind is able to talk to another person in a noisy environment without having to remove the hearing protector and without risking any hearing damage. The electronic unit may also be designed to have both of the functions described above.

Different types of ear cups may be designed with different degrees of attenuation depending on the levels of noise in the environments in which they are to be used. If a hearing protector is intended for use in environments where noise levels are high, for example in the vicinity of aircraft taking off, the ear cup must have a much higher degree of noise attenuation than if the hearing protector is to be used in less noisy environments, for example in a catering kitchen. For this reason, hearing protectors are designed to have different noise-attenuating ability, i.e. to have noise-reducing spaces of different size. In general, the larger the cup the better the attenuating ability.

It is important that speakers arranged in hearing protectors do not emit sound that is too loud, so that it becomes harmful to the ear of the user. For this reason, there is an upper limit for the sound volume that can be emitted by the electronic unit through the speaker in the ear cup. This sound reproduction level limit is described, for instance, in the European standard EN352. To avoid that the sound level emitted by the speaker adjacent the ear of a user exceeds this limit, and to make sure that the user has the same type of sound experience with all ear cups, it is desirable for active ear cups to emit the same sound level adjacent the ear at a certain sound volume setting, independently of the type of ear cup. To achieve this in cups with different degrees of attenuation, i.e. with noise-reducing spaces of different size, different electronic circuitry must be employed today to provide the same sound-reproducing function(s) depending on the degree of attenuation of the ear cup. When manufacturing, for example, ear cups with two different degrees of attenuation, two versions of the circuitry required to provide the sound-reproducing function must be developed, one for the ear cup with a higher degree of attenuation and another for the ear cup with a lower degree of attenuation. This means higher costs for each ear cup in the form of assembly, development, adaptation of the circuitry, storage etc. than would be the case if the same circuitry could be used regardless of the degree of attenuation of the ear cup.

SUMMARY OF THE INVENTION

An object of the present invention is therefore to provide a solution that eliminates the drawback described above, i.e. that provides a similar sound experience adjacent the ear of a user with the same type of electronic circuitry and speaker regardless of the size and degree of attenuation of the ear cup.

The object is achieved by a system for forming hearing protectors, an ear cup in such a system and a hearing protector formed from such a system according to the respective independent claims.

Embodiments of the invention appear from the dependent claims and from the following description and the appended drawings.

According to a first aspect of the invention, this object is achieved by a system for forming hearing protectors, which comprises at least one first ear cup (5a) and at least one second ear cup (5b), the first and second ear cups having noise-reducing spaces (11) of different size, and at least one electronic unit (30) with at least one speaker (31), the ear cups (5a, 5b) being arranged to accommodate the electronic unit, each of the ear cups (5a, 5b) being arranged to accommodate the speaker (31) in such a manner that an inner distance (l) is obtained in the noise-reducing space (11) from the speaker and in the direction of the ear of a user, when the user is wearing the ear cup, the ear cups (5a, 5b) further having a resonance space (15), which is arranged to function as a sounding board for sound emitted by the speaker (31), and the inner distance ($1_a$) and the volume of the resonance space ($V_a$) in the first ear cup (5a) being adapted to the inner distance ($1_b$) and the volume of the resonance space ($V_b$) in the second ear cup (5b) such that, when the electronic unit (30) is mounted in each ear cup (5a, 5b), sound emitted by the speaker (31) in each ear cup produces substantially the same sound characteristic from the first ear cup (5a) as that from the second ear cup (5b).

The noise-reducing space can be defined as a space that is limited by the inside of the ear cup and a surface that is defined by an outer, circumferential edge on the ear cup, which edge is adapted to face the ear of a user.

By "inner distance" is meant the distance that sound emitted by a speaker arranged in an ear cup travels inside the noise-reducing space from the speaker, suitably the speaker diaphragm, until it leaves the noise-reducing space in the direction of the ear of a user, when the ear cup is positioned against the ear of the user. This distance is suitably defined as the distance from the speaker diaphragm to a surface that is defined by the outer, circumferential edge of the ear cup. See reference numerals $1_a$, $I_b$ in FIGS. 2a, 3a.

By "resonance space" is meant the spatial cavity in the ear cup that is intended to act as a sounding board for sound emitted by speakers, i.e. the space adjacent the speaker that has a substantial impact on the emitted sound level and sound characteristic. The resonance space is primarily located behind the speaker, and is also called the rear volume of the speaker.

Suitable inner distances and volumes of the resonance space are determined by laboratory testing for each type of ear cup by varying the position of the speaker in each cup and by varying the volume of the resonator space until substantially the same sound characteristic is obtained for one type of cup with a noise-reducing space of a certain size as for another type of cup having a noise-reducing space of a different size, when using the same type of speaker and electronic circuitry in both cups. By employing this solution, there is no need to have different circuitry for different ear cup sizes. As a result, cups are more cost-efficient due to reduced costs for assembly, development, adaptation of circuitry, storage etc than would be the case if different circuitry would have to be used for different ear cup sizes.

According to one embodiment of the invention, the ear cups have a support, which is arranged in the noise-reducing space and on which support the speaker is to be mounted. This makes it possible to change the inner distance and the volume of the resonance space, respectively, in the ear cups by altering the extension of the support in the direction in which sound emitted by a speaker arranged on the support would travel in the direction of the ear of a user, to obtain substantially the same sound characteristic in two different ear cups with noise-reducing spaces of different size.

According to another embodiment, the resonance space in each ear cup is formed by at least part of the noise-reducing space.

According to a further embodiment, the resonance space in each ear cup is designed such that it is separated from the noise-reducing space when the speaker is mounted in an ear cup. A clearly delimited resonance space is thus obtained the volume of which can be changed relatively easily to achieve the object of the invention. Furthermore, this makes it relatively easy to provide a resonance space of the same size in both the right and the left ear cup of a hearing protector, since the size of the resonance space is not dependent on the size of the noise-reducing space, which size may not be the same in the right ear cup and in the left ear cup depending on whether any elements are arranged in the noise-reducing space in the right or left ear cup.

According to yet another embodiment of the invention, the support is formed with a recess and this recess forms the resonance space in the ear cup. This allows both the inner distance and the volume of the resonance space to be changed by designing the support in different ways, which makes it easier to adjust these measures to match ear cups of different sizes, thereby to achieve the object of the invention. Moreover, the size of the resonance space will not be dependent on the size of the noise-reducing space, which gives the same advantages as those of the previous embodiment.

According to another embodiment, the support in each ear cup is arranged such that when the speaker is mounted on the support the recess is covered in a manner that separates it completely from the noise-reducing space. Because the space behind the speaker is separated from the space in front of the speaker, the risk that sound emitted by the speaker will affect the speaker itself through acoustic short-circuiting is eliminated. Furthermore, a closed space of this kind behind the speaker gives a better bass sound in the speaker than if the resonant volume and the noise-reducing space are partly the same volume.

According to another embodiment, the inner distance ($1_a$) in the first ear cup is substantially the same as the inner distance ($1_b$) in the second ear cup and the volume ($V_3$) of the resonance space in the first ear cup is substantially the same as the volume ($V_b$) of the resonance space in the second ear cup. By the measures being the same in the two different variants of ear cups with noise-reducing spaces of different size, the sound characteristic is substantially the same adjacent the ear of a user from both ear cups when similar circuitry is used in both ear cups.

According to a further embodiment, the ear cups each have an inner cup portion, which defines the noise-reducing space and an outer cup portion, which is arranged to accommodate at least a part of the electronic unit. By dividing the cup in two in this way, it is possible to provide a noise-reducing space of the same size in both the right ear cup and the left ear cup of a hearing protector, regardless of whether the electronic unit is arranged in only one of the ear cups or, for example, split in such a manner that the electronic circuitry as such is arranged in one of the ear cups of the hearing protector and the battery of the electronic unit is arranged in the other ear cup of the hearing protector.

The invention also concerns an ear cup included in the system and a hearing protector made up of some of the parts of the system.

BRIEF DESCRIPTION OF THE DRAWINGS

FIG. 2b is a perspective view of the ear cup in FIG. 2a.

FIG. 2c is a front view of the inside of the ear cup in FIG. 2a.

FIG. 3b is a perspective view of the ear cup in FIG. 3a. FIG. 3c is a front view of the inside of the ear cup in FIG. 3a.

DESCRIPTION OF PREFERRED EMBODIMENTS

Figure 1:
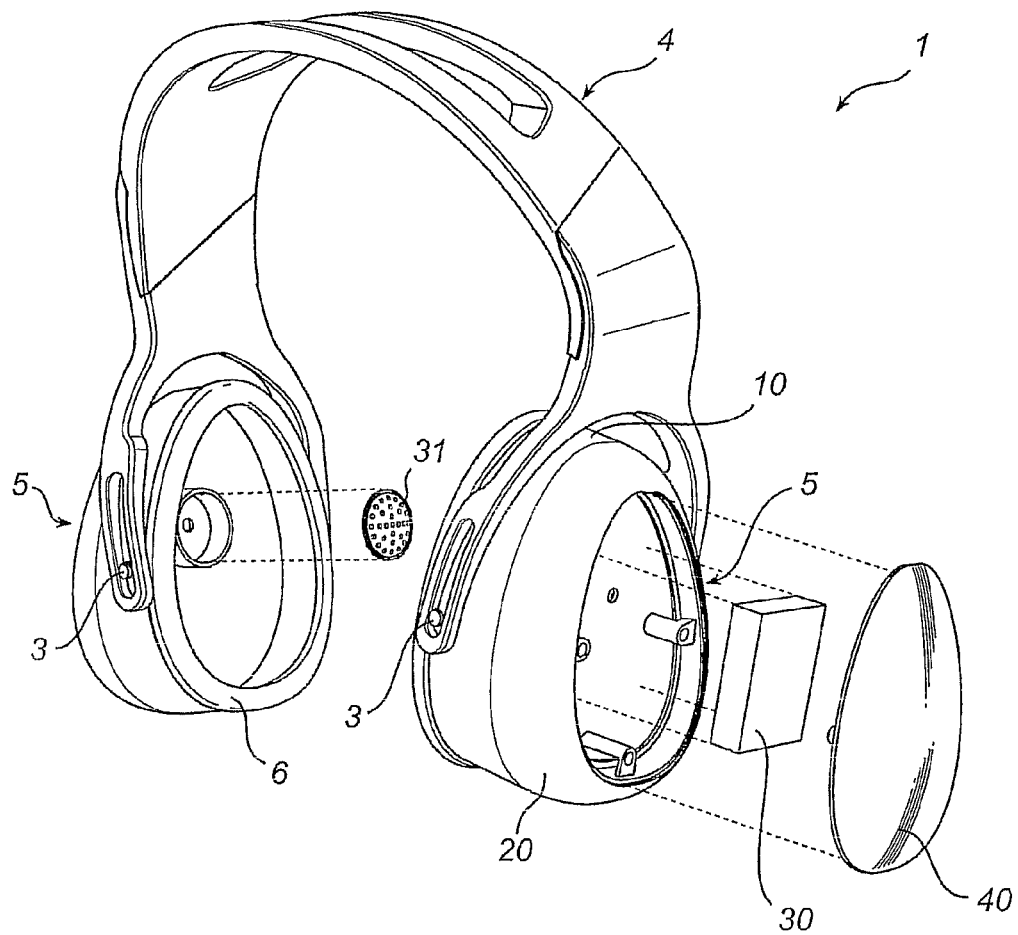
FIG. 1 is a perspective view of a hearing protector in which the electronic circuitry, including speakers and lids, is illustrated in the form of an exploded view.

FIG. 1 shows a hearing protector 1 which has two ear cups 5. The ear cups are connected to each other by a strap 4 for mounting the hearing protector on the head of a user. The strap is fastened to the ear cups with the aid of fastening devices 3. In one alternative embodiment, instead of the strap 4 the two ear cups 5 may have another device for connecting the ear cups with each other, for example each of the cups may be provided with a holder, which is provided for attachment to a helmet or the like which is to be worn on the head of a user. Each of the ear cups 5 has an inner cup portion 10 and an outer cup portion 20, which are made of, for example, rigid plastic. Mounted on the edge 12 of the inner cup portion (see for example FIG. 2b) is a sealing ring 6, which is arranged to be in close contact with the head of a user in the area around one ear of the user. Advantageously, the ear cups 5 have noise-reducing spaces of equal size, so that the reduction of noise is the same for the right ear and for the left ear of the user.

Figure 2C:
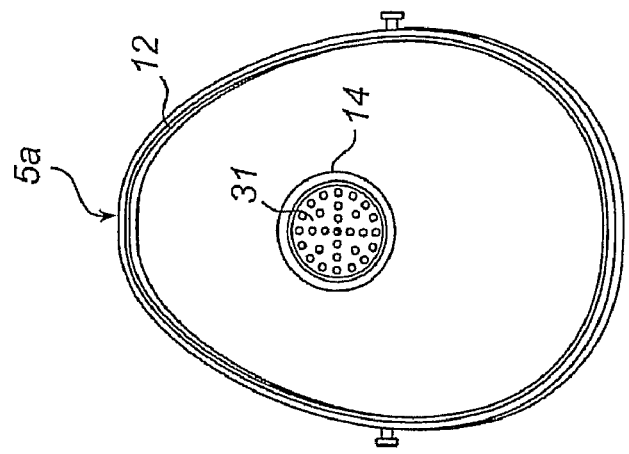
Figure 2B:
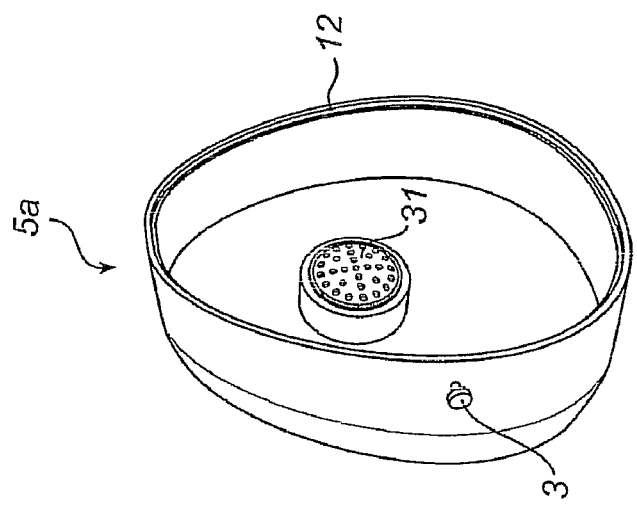
Figure 2A:
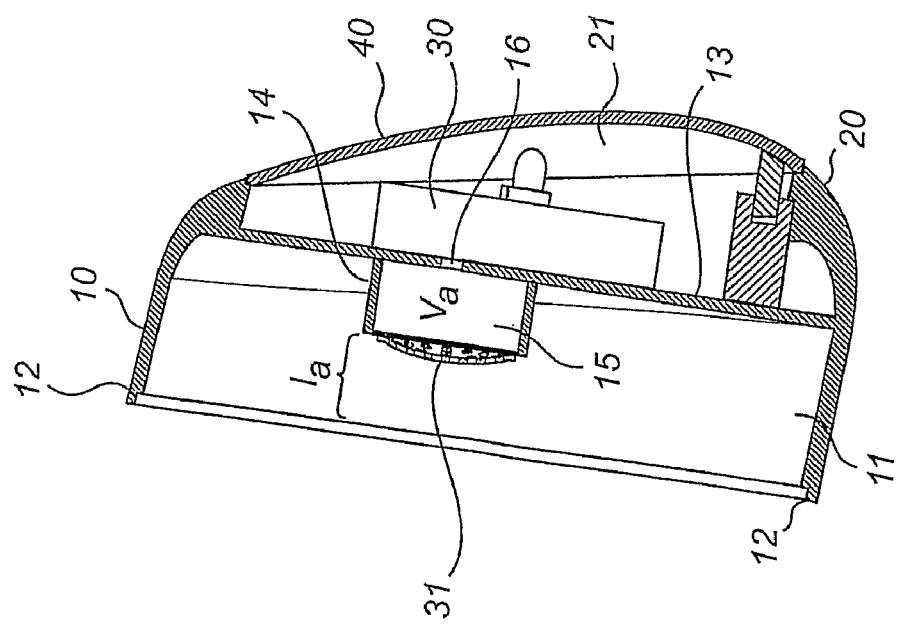
FIG. 2a is a cross-sectional side view of an ear cup with a large noise-reducing space, in which the electronic circuitry, including a speaker, is mounted.
Figure 3C:
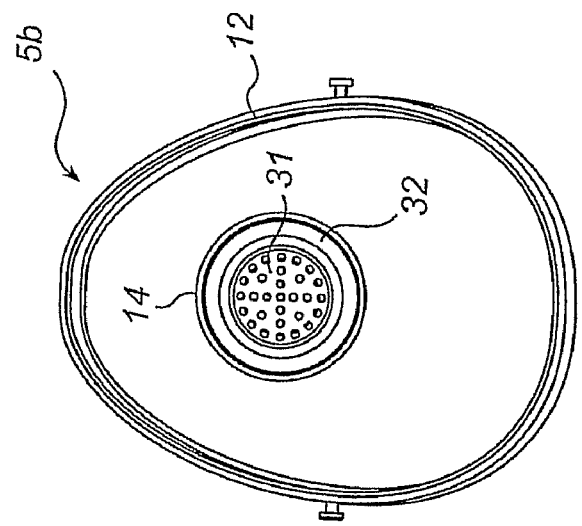
Figure 3B:
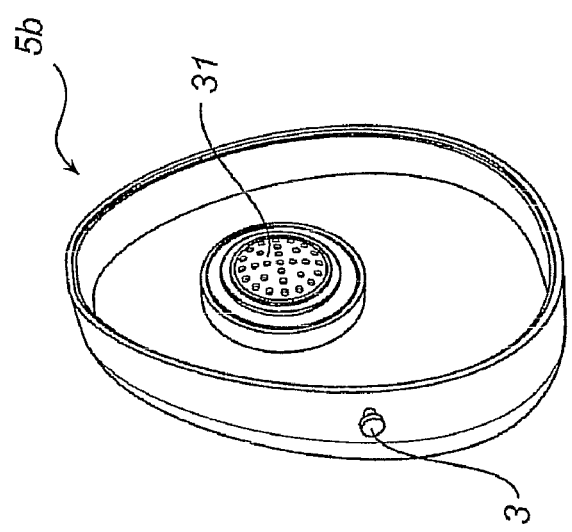
Figure 3A:
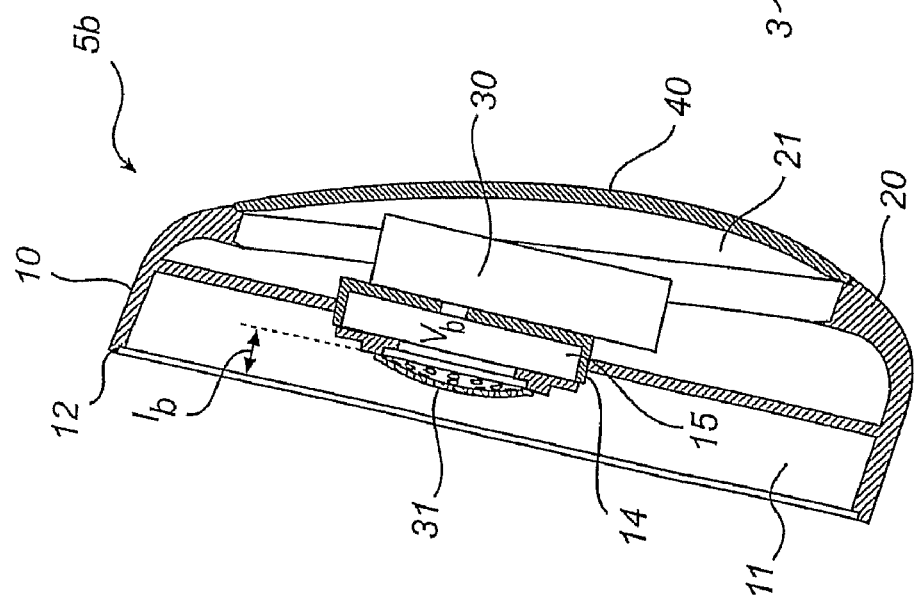
FIG. 3a is a cross-sectional side view of an ear cup with a small noise-reducing space, in which the electronic circuitry, including a speaker, is mounted.

FIGS. 2a-2c show a first ear cup 5a with a large noise-reducing space 11 and FIGS. 3a-3c show a second ear cup 5b with a small noise-reducing space 11. Both the first and the second ear cup have the features described below.

The inner cup portion 10 delimits the noise-reducing space 11. The inner cup portion 10 has an outer, circumferential edge 12, which is arranged to face the user when the user is wearing the ear cup. The outer, circumferential edge 12 is designed such that it allows the arrangement of a sealing ring thereon. The outer cup portion 20 and a lid 40 define an outer space 21 intended to accommodate, inter alia, parts of an electronic unit 30. The electronic unit comprises: electronic circuitry for providing a sound-reproducing function, for example an FM radio, and/or an mp3 player and/or electronic circuitry for reproducing ambient sound; at least one speaker and a current source. In a hearing protector, the electronic unit is either mounted in one of the ear cups or split between both ear cups, for example by the current source being arranged in one ear cup and the circuitry in the other ear cup. Speakers are advantageously arranged such that there is one speaker in each ear cup.

The inner cup portion 10 and the outer cup portion 20 are separated by a partition 13, which may be made in one piece with the inner cup portion 10. In the noise-reducing space 11, a support 14 which extends from the partition is arranged to accommodate a speaker 31. The support has a recess 15, which forms a resonance space for the speaker. The support 14 and the speaker 31 are designed in such manner that when the speaker is mounted on the support 14 the recess 15 is sealed by the speaker, so that the resonance space formed is separated from the noise-reducing space 11. The partition 13 further has a hole 16 through which a wire (not shown) connecting the speaker 31 to the electronic circuitry 30 is passed.

According to the invention, the first ear cup 5a is formed with a large noise-reducing space 11 and the second ear cup 5b with a small noise-reducing space 11, so that an inner distance I is obtained from the speaker when mounted on the support 14 to a surface defined by the circumferential edge 12. This inner distance $1_a$ in the first cup 5a and the volume $V_3$ of the resonance space 15 of the first cup are then adjusted to match the corresponding inner distance $1_b$ and volume $V_b$ of the second cup 5b, so that when the same type of electronic circuitry 30 is arranged in the first cup 5a and the second cup 5b, respectively, substantially the same sound characteristic is obtained at the surface defined by the circumferential edge 12 for sound emitted by a speaker 31 mounted on the support 14. The adjustment is made by testing different distances and resonance space volumes until a ratio is found which gives substantially the same sound characteristic for both ear cups.

In one embodiment, the first and the second ear cup are designed such that the inner distance $1_a$ in the first ear cup is substantially the same as the inner distance $I_b$ in the second ear cup, and that volume $V_a$ of the resonance space in the first ear cup 5a is substantially the same as the volume $V_b$ of the resonance space 15 in the second ear cup 5b. As a result, the sound characteristic is substantially the same adjacent the ear of a user. To achieve the same resonance space volume and, at the same time, the same inner distance in cups with noise-reducing spaces 11 of different size, the speaker must be located further away from the inside of the noise-reducing space (i.e. the surface of the partition 13) in the first cup 5a than in the second cup 5b for the speaker to be located at the same distance from the surface defined by the circumferential edge 12 in both the first and the second cup. Accordingly, the support 14 is made higher, i.e. it has a greater extension length in the first cup 5a than in the second cup 5b. In this connection, the resonance space 15 is adapted so that it has the same size in the first cup 5a as in the second cup 5b.

According to one embodiment, which is illustrated in FIGS. 2a and 3a, the support 14 may have the form of a cylinder which rests on the inside of the inner cup portion 10, against the partition 13, and extends towards the surface defined by the circumferential edge 12. The cylinder has an upper surface located furthest away from the partition, which face forms an bearing surface for the speaker, in that the speaker is adapted to be arranged on this bearing surface. The resonance space 15 is thus formed by the space delimited by the cylinder 14, the partition 13 and the surface defined by the bearing surface. In the embodiment where the first and the second cup have the same inner distances I and volumes of the resonance space V, the resonance space is then Banned such that the cylinder 14 of the first ear cup 5a with a larger noise-reducing space 11 has a greater extension and more narrow cross-sectional area than that of the second ear cup 5b with a smaller noise-reducing space. In this way, the cups will have the same inner distances I and the same volumes of the resonance space V.

The invention also concerns a system for forming a hearing protector. The system comprises a number first ear cups 5a with a large noise-reducing space 11, a number of second ear cups 5b with a small noise-reducing space 11 and a number of electronic units 30 of the same type with at least one speaker 31 each. To form a hearing protector from this system, two copies of the same type of ear cup, two speakers and one electronic unit are advantageously selected, which are then assembled. For example, a hearing protector for use in extremely noisy environments is, suitably made up of two copies of the first ear cup with a large noise-reducing space and an electronic unit with two speakers, one for each ear cup. In the same way, a hearing protector intended for less noisy environments is suitably made up of two units of the second ear cup with a small noise-reducing space and an electronic unit with two speakers, one for each ear cup, the electronic unit, including the speakers, being of the same type for both hearing protectors.

Figure 4:
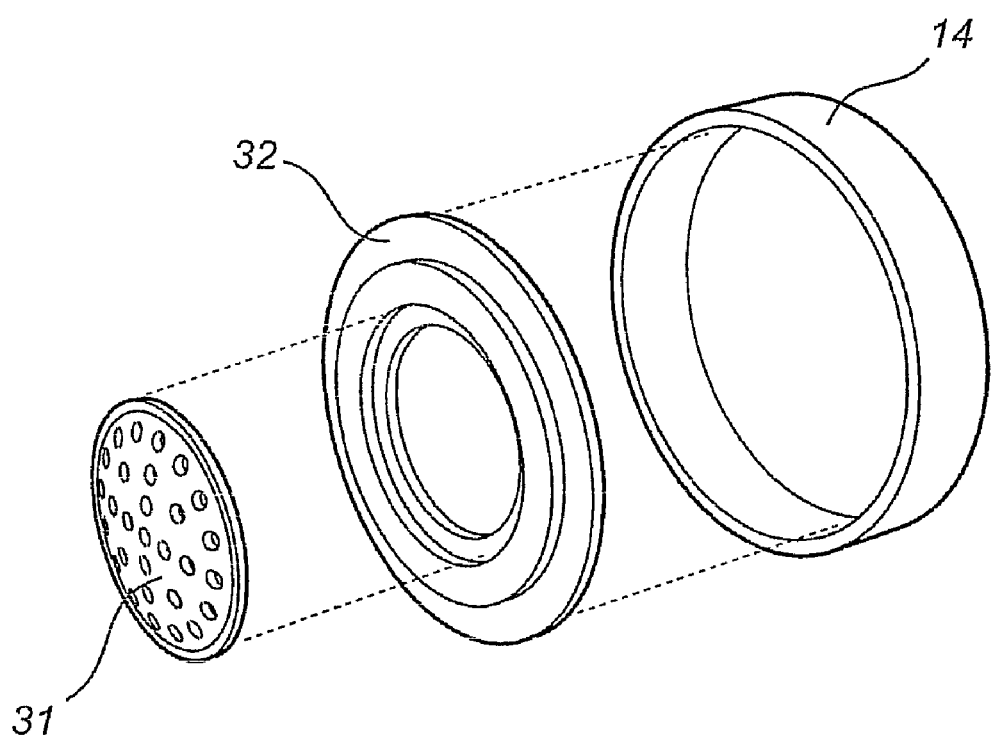
FIG. 4 is an exploded view of part of an ear cup and a speaker.

The system does not exclude forming of hearing protectors comprising a first ear cup with a large noise-reducing space and a second ear cup with a small noise-reducing space and an electronic unit with two speakers. It is also conceivable to have embodiments of hearing protectors in which only one of the ear cups is equipped with speakers, and thus acts as a passive ear cup. As well as having two different types of ear cups, the system may also have three or more types of ear cups of different size, which can be used to form hearing protectors with a large number of noise-reducing spaces of different size and, thus, with different noise-reducing abilities. As described above, the same type of speaker may be used in cups with noise-reducing spaces of different size. FIG. 4 shows how a speaker can be adapted for mounting on supports of different sizes. FIG. 4 illustrates, in the form of an exploded view, the speaker 31, a sealing ring 32 and the support. By using an adapter device, which may be, for example, a sealing ring 32, the size of the speaker 31 can be adapted. The sealing ring 32 is provided in different sizes depending on the size of the support 14, to allow mounting of the speaker on the support. Advantageously, the sealing ring is designed such that when the sealing ring 32 has received the speaker 31 and they have been positioned on the support 14, the speaker and the sealing ring 32 cover the recess 15 in the support 14 regardless of the cross-sectional area of the recess 15, which results in the recess 15 that forms the resonance space being separated from the noise-reducing space. This allows the same type of speaker to be used for different types of ear cups regardless of the size of the support.

In one alternative embodiment, the ear cup may be formed without a separate resonance space. In this case, the whole noise-reducing space, or at least the part of the noise-reducing space that is located behind the speaker, serves as a resonance space. In this case, the ear cup may be designed, for example, such that the speaker is mounted on a support in the form of two pins on which the speaker rests.

In another alternative embodiment, the cups may have a single cup portion, in which the electronic circuitry is to be mounted in the noise-reducing space.

What is claimed is:

1. A system for forming hearing protectors, comprising:
at least one first ear cup and at least one second ear cup, the first and second ear cups each having an outer cup portion and an inner cup portion, a partition separating the outer cup portion and the inner cup portion, a noise-reducing space defined entirely within the inner cup portion, and at least one electronic unit with at least one speaker, wherein the noise reducing space of the at least one first ear cup is a different size than the noise reducing space of the at least one second ear cup,
the ear cups being arranged to accommodate the electronic unit,
each of the ear cups being arranged to accommodate the speaker in such a manner that an inner distance is obtained in the noise-reducing space from the speaker and in the direction of the ear of a user, when the user is wearing the ear cup,
the ear cups further having a resonance space, which is arranged to function as a sounding board for sound emitted by the speaker, and
the inner distance and the volume of the resonance space of the first ear cup being adapted to the inner distance and the volume of the resonance space of the second ear cup such that, when the electronic unit is mounted in each ear cup, sound emitted by the speaker in each ear cup produces substantially the same sound characteristic from the first ear cup as that from the second ear cup.

2. A system according to claim 1, wherein each ear cup has an outer, circumferential edge, which is arranged to face the ear of a user, the inside of the cup and a surface defined by the outer, circumferential edge defining the noise-reducing space,
and the inner distance is a distance from the speaker to the surface defined by the outer, circumferential edge.

3. A system according to claim 1, wherein each ear cup has a support which is arranged in the noise-reducing, space, on which support the speaker is to be arranged.

4. A system according to claim 1, wherein the resonance space in each ear cup is formed by at least part of the noise-reducing space.

5. A system according to claim 3, wherein the resonance space in each ear cup is designed such that it is separated from the noise-reducing space when the speaker is mounted in an ear cup.

6. A system according claim 3, wherein the support in each ear cup has a recess and this recess forms the resonance space in the ear cup.

7. A system according to claim 6, wherein the support in each ear cup is so arranged that when the speaker is mounted on the support the recess is covered in a manner that separates it completely from the noise-reducing space.

8. A system according to claim 1, wherein the inner distance in the first ear cup is substantially the same as the inner distance in the second ear cup, and the volume of the resonance space in the first ear cup is substantially the same as the volume of the resonance space in the second ear cup.

9. A system according to claim 1, wherein at least one of the at least one first ear cup and the at least one second ear cup has an inner cup portion, which defines the noise-reducing space and an outer cup portion which is arranged to accommodate at least a part of the electronic unit.

10. The system according to claim 1, further comprising an ear cup.

* * * * *